United States Patent [19]
Sato et al.

[11] Patent Number: 6,160,206
[45] Date of Patent: Dec. 12, 2000

[54] PORPHYRIN-ACCUMULATING TYPE HERBICIDE RESISTANCE GENE

[75] Inventors: Ryo Sato, Funabashi, Japan; John Boynton, Durham, N.C.; Nicholas W. Gillham, Durham, N.C.; Elizabeth H. Harris, Durham, N.C.

[73] Assignees: Sumitomo Chemical Company, Ltd., Osaka, Japan; Duke University, Durham, N.C.

[21] Appl. No.: 09/009,119

[22] Filed: Jan. 20, 1998

Related U.S. Application Data

[63] Continuation of application No. PCT/US96/11999, Jul. 19, 1996, abandoned, which is a continuation-in-part of application No. PCT/US95/09098, Jul. 20, 1995, abandoned.

[51] Int. Cl.$^7$ .............................. C12N 5/04; C12N 15/82; A01H 5/00; A01H 5/10
[52] U.S. Cl. ................... 800/300; 536/231.1; 800/278; 800/290; 800/298; 435/69.1; 435/70.1; 435/71.1; 435/471; 435/410; 435/411; 435/418; 435/419
[58] Field of Search .................. 536/231.1; 800/278, 800/290, 300, 298; 435/69.1, 70.1, 71.1, 471, 410, 411, 418, 419

[56] References Cited

FOREIGN PATENT DOCUMENTS

WO9534659A1 12/1995 WIPO.
WO9732011 9/1997 WIPO.
WO9732028 9/1997 WIPO.

OTHER PUBLICATIONS

Sato et al., Am. Chem. Soc. Symposium Series 559:91–104(1994).
Oshio et al., Zeitschrift Fur Naturforschung 48:339–344 (1993).
Kataoka et al., J. Pesticide Science 15:449–451 (1990).
Shibata et al., Research in photosynthesis 3;567–570(1992).
Sato et al., Abstracts of ACS Nat'l meeting; Abstr. #112 (1993).
Pornprom et al., Pesticide Biochemistry and Physiology 50: 107–114 (1994).
Takahashi et al. The EMBO J. 1991. vol. 10:2033–2040.
Napoli et al. The Plant Cell. 1989. vol. 2: 278–289.
Tapperman et al. Plant Molecular Biology. 1990. vol. 14: 501–511.
Sato et al. Am. Chem. Soc. Symposium Series. 1994. vol. 559: 91–104.
Shibata et al. Research in Photosynthesis. vol. III. pp. 567–570. Edited by Murata, 1992.
Gordon–Kam et al. The Plant cell. 1990. vol. 2: 603–618.

*Primary Examiner*—Lynette R. F. Smith
*Assistant Examiner*—Ousama M-Faiz Zaghmout
*Attorney, Agent, or Firm*—Birch, Stewart, Kolasch & Birch, LLP

[57] ABSTRACT

Provided are DNA fragments and biologically functional equivalents thereof that confer resistance to porphyrin-accumulating type herbicides upon plant and algal cells, plasmids containing these DNA fragments or biologically functional equivalents thereof, microorganisms containing these DNA fragments or biologically functional equivalents thereof, methods for conferring resistance to porphyrin-accumulating type herbicides upon plant or algal cells using these DNA fragments or biologically functional equivalents thereof, and herbicide-resistant plants or algae into which these DNA fragments or biologically functional equivalents thereof have been introduced and in which they are expressed.

7 Claims, 4 Drawing Sheets

6,160,206

SEQUENCE LISTING

```
<160> NUMBER OF SEQ ID NOS: 1

<210> SEQ ID NO 1
<211> LENGTH: 3381
<212> TYPE: DNA
<213> ORGANISM: Chlamydomonas reinhardtii

<400> SEQUENCE: 1
ctcgagttgg cattgttagt cttaagcatc ttcgaaacca tggcacttat gggcgaagcc      60
gcaacataca cctgacgatg ctcccctgcc ctcctcttcc caccacggaa gcaacccatg     120
caattggtct ttcgcttgtg cactgacagt caatgccttg ggtctggccc cctgctccgg     180
gtattcgcaa tttatagccc cctttttgaag gtacttcgag acctagtcta tgtcactcag    240
ttctgtgtct ctcctgtgct atgctgggac cacactgagg gacagtgccc ccaaaccgcc     300
ccgcgtgtgc gccaactcac tctcgccaaa acttcatgca aacaatgcac aacggggctg     360
tacaacggag cgtcatagtg cagttaaccc gcacataacg gtgccgacag agctttacca    420
```

-continued

```
accacatcgc tcatcccagc accacctatg tccttggcag acccccgaac ccctagctcc      480
acatccccga tccattccaa ctgttactac acatcccagc aagcgccaat ggtagccccc      540
ccctcgcctc cactccgctt gccccaagtg cttgccaatt gctgctgccg gtgccactgc      600
ggcatttacc agctacagcc cgatgctgct gctgctactg ctgcagccgc ttaggccttg      660
actgcggcct tggacacgct cttggccagg ttggctgcgg actcgtagcc gtgctccacc      720
accttgccca gggccacacc tggttgcagg ggttcgaggg gggagagggg ccgaggggt      780 tggggatgag gcaaaggcgt gggcacacgt gtgggcgggg ggcggctggg cggctgggca      840
ccatacagcg aagggccag ggggggtcatg tgcccgagcc caacgaaata ggtcccaata      900
gtcaaggaat catcgcccgc gtcgggggta gtcatacatg tagcctccgc tccttgcagt      960
cccctgacct cttgttcatg ctgggtttcc cggtttcagt caatgaggat acaacaccgc     1020
cttgctttgc gccttagcac cacctcctgc tcaacctcct ccttgtaccc tcccctcccc     1080 tccctcccc tcttcctgct gctgctgctg cccacgcgct caccgctgac gtagttgccc     1140
cccaggtgca cgccctgcag ccccgccgcg tccagcgcct tgcgcgcctt gtccagctgc     1200
tccaggtggc ccaggttgaa ctgcaggtgg cagggcgggg aggaggggtt acacatgcag     1260
cccaaactaa accgaaccta atgcaaagag tggtacagag aagtgcagca aagtatacaa     1320
caggtgaagt tgattccaga acccaaaagc aagtcaaccg agtgaaccca aatccgggga     1380
gaggtggcta ggttgggagg gggcagccag gttatcaggt cgaaggtcgc aggtcgaggt     1440
tatagggctg tagagctctt tgagaaacta ggatctagcc catccctccg gctgctgcgc     1500
cctcacacct gcgggatggc gcgcggccac acgcgcacgc ccaccacacg gggcttgggc     1560
gcgtcgggct tgatgaccat gttgcgcagg tccttgtcca cctgcaggga gatggggtgg     1620
ggggagaggc ggtgagagca ggcgtgcggc agggggggg gtgcggcagg tggaagacgt     1680
ggaacgggcg gcggggttcg gggctgcagg acgaaaatgt gtgtgtgtgt gtgtgtgtgt     1740
gtgtgtgtgt gtgtgtgtgt gtgtgtgtgt gtgtgtgtgt gtgtgtgtgt gtgtgtgtgt     1800
gtgtgtgtgt gtgtgtgtgt gtgtgcgtgt gtgtgcccac aggggggttct ggccagctcc     1860 gaagcaacac gggtccaaga cgccacacaa caagggggtgt cagctttgta cagctggaaa     1920
atgggctgag cccatgtag cgcaaggga tgtgacgatg ggcaccggcg acatgaacag      1980 caccccttgca agcccatcca gcgggactgg ccactaggcc aacgctgtgc cgaggcaccg      2040
acatgccctg tccccgccac gccacgccac cttacccacg ccacttcacg gtccatgata      2100
tcccaaatgc acctcaccca catcccactc aagcaccgca aagggctagc cgggctcggg      2160
cgcgggatcc cggccgcga cacatgtaag gctcggggac gcatggtttg gctgttgcaa      2220
acaatttcga cattcttgcc ccaagacgct tgtcgtcgac atgttttgat acatggatgt      2280
aagatattta ggggccgaga gctatactcg cgaactgaag aaagtcaaga tgtccatgga      2340
ctcacgaggt cgcttctcgc tccggccgag ttttccctgc cgtctatttt tctacaatag      2400
gtaattgcaa ttaataatac gtggcactcg cggtttgtgc cagtacggta ctttttgtcg      2460
acacaggcac acacgcacgc acggacaggg gcaatcctgg ggggcttcgc ccccctgga     2520 tcgctttgct caggggctc agcccaaaaa tccactgccc cccccccacc ccccacaca      2580 cacacctgct ccaccagctg ctcggtggtc tggttgacga tgccgcggtt ggtggtgccg      2640
ccgatgtagt tgagcagcag catgtggccc tcgggcgcgc ggccggggaa caggctggag      2700
ctgtagatgg tgcccagagt ggtgatgccc tgtgtgtgga caagtgtgtg tgttagaaga      2760
caccaaaatg aagcgaagag tgtgttaagg agcaccagac aaagtaagcg caaagagggt      2820
```

-continued

```
gcgtgtgcgc ccgtgtgtgt tgttgaaggg gggaatggat gaggggagcg cgaggataca    2880
accgcgggat acgacccagc gccccaatcc cccccacccc caccccaac ccccaccacc     2940 ctcccctccg caacacaccg cccgcaacac gcgcgcactt gcccacctgc gtgcgcgggt    3000
gcagctgacc gaagcccggc acggacccgt ccgaggcctt gcgctcctcc cgcacggcgc    3060
tcagcgggta cgacagcgtc acggcgccca tcggcgggta gtcgaaggag cccagggcct    3120
cggcggcggc gggctgtgcg ggggggagag ggagggaggg gcaggcgcag ggaggcgggg    3180
ttacgttaat gattgcccaa gaaactggta gacggtagac agtctaggtg ggggaggagg    3240
agcggatgga atcgggatgg agccgaggag tggaaggggc agtaaagccg gggggagcg    3300 ggtagcagga aaggggggacg tggccgtgca cacaaagaag ccggaacagg tgccaaacgg  3360
atttcctcca acgctctcga g                                              3381
```

PORPHYRIN-ACCUMULATING TYPE HERBICIDE RESISTANCE GENE

RELATED APPLICATION

The present application is a continuation of PCT International application No. PCT/US96/11999, filed on Jul. 19, 1996 which designated in United States, which is a Continuation-in-Part of PCT/International Application No. PCT/US95/09098, filed on Jul. 20, 1995, which designated the United States. The entire contents of both of these application are hereby incorporated by reference.

BACKGROUND OF THE INVENTION

1. Field of the Invention

The present invention relates to DNA fragments that confer resistance to porphyrin-accumulating type herbicides on plant and algal cells, plasmids and microorganisms that contain these DNA fragments, methods for conferring resistance to porphyrin-accumulating type herbicides onto plant and algal cells by using these DNA fragments, and plants and algae into which these DNA fragments have been introduced for the purpose of conferring resistance to such herbicides thereon.

2. Description of Related Art

A group of widely-known compounds used as active ingredients of some varieties of commercially- and otherwise-available herbicides exhibit herbicidal activity in the presence of light, but exhibit no herbicidal activity in darkness. This has led to their common designation as light-dependent or porphyric herbicides. It has recently been shown that these herbicides induce high levels of porphyrin accumulation in plants and algae, and thus they are now designated as "porphyrin-accumulating type herbicides" [Zoku,Iyakuhin-no-Kaihatsu, (translation: "The Development of Medical Drug Products; continuation") vol. 18; Development of Agricultural Chemicals II, chapter 16, section 16-1, Hajime Iwamura, Tamio Ueno & Katsuzo Kamoshita, eds., Hirokawa Shoten, Tokyo, pubs.) or simply "porphyric herbicides". It was reported by Matringe, M., Camadro, J. M., Labbe, P. & Scalla, R. (*Biochem J.* 260:231 (1989)) and by Matringe, M., Camadro, J. M., Labbe, P. & Scalla, R. (*FEBS Lett.* 245:35 (1989)) that porphyrin-accumulating type herbicides (referred to below also as porphyric herbicides) inhibit isolated protopor-phyrinogen oxidase (referred to below as "protox").

Since most crop plants do not exhibit resistance to these porphyric herbicides, it is not possible to use these herbicides on farmland when such crops are under cultivation. If it were possible to develop crops resistant to porphyric herbicides, such herbicides could be used on these crops. This would make crop management easier, and increase the value of these herbicides in agricultural applications. For this reason, it is desirable to develop a method for conferring resistance to porphyrin-accumulating type herbicides upon crop plants.

SUMMARY OF THE INVENTION

With this goal in mind, the present inventors have investigated a mutant strain, designated RS-3, of the unicellular green alga *Chlamydomonas reinhardtii* which displays specific resistance to porphyric herbicides. Wild-type strains of this alga are normally highly sensitive to porphyric herbicides. The present inventors have discovered that inhibition by porphyric herbicides of protox activity in chloroplast fragments isolated from the RS-3 strain of *Chlamydomonas reinhardtii* was significantly lower than in chloroplast fragments from the wild-type strain. The inventors therefore constructed a genomic DNA library from total nuclear DNA isolated from the RS-3 mutant strain, and succeeded in isolating clones that contain a gene responsible for resistance to porphyric herbicides. Thus, the inventors were able to obtain DNA fragments that can confer resistance to porphyrin-accumulating type herbicides onto plant and algal cells.

Accordingly, it is an object of the present invention to provide an isolated, purified DNA fragment that confers resistance to porphyrin-accumulating type herbicides when expressed in plant or algal cells, plasmids and microorganisms containing said DNA fragment. A DNA fragment according to the present invention preferably has a nucleotide sequence of one or more portions of DNA comprising the genome of an alga, or has a nucleotide sequence highly homologous to the nucleotide sequence of DNA comprising one or more portions of the genome of an alga.

Additional objects of the present invention are a method for conferring resistance to porphyrin-accumulating type herbicides upon plant or algal cells, comprising introducing said DNA fragment into said plant or algal cells, wherein said DNA fragment is expressed; and plants or algae into which said DNA fragment has been introduced, wherein said DNA fragment is expressed, thereby conferring herbicide resistance upon said plants or algae.

Another object of the present invention is to provide an isolated, purified DNA fragment having the following characteristics:

a) comprising a nucleotide sequence derived from a DNA fragment obtained from a strain of the unicellular green alga *Chlamydomonas reinhardtii* that exhibits resistance to porphyrin-accumulating type herbicides;

b) containing restriction sites for XhoI, PstI, PstI, PstI, PstI, PstI, BamHI, SalI, SalI, and XhoI, and having a restriction site map as shown in FIG. 1(*a*);

c) having a molecular size of approximately 3.4 kb; and d) which confers resistance to porphyrin-accumulating type herbicides in plant or algal cells when expressed therein, or a biologically functional equivalent thereof.

A further object of the present invention is to provide an isolated, purified DNA fragment having the following characteristics:

a) comprising a nucleotide sequence derived from a DNA fragment obtained from a strain of the unicellular green alga *Chlamydomonas reinhardtii* that exhibits resistance to porphyrin-accumulating type herbicides;

b) containing restriction sites for EcoRI, XhoI, PstI, PstI, PstI, PstI, PstI, BamHI, SalI, SalI, XhoI and HindIII, and having a restriction site map as shown in FIG. 1(*b*);

c) having a molecular size of approximately 9.9 kB; and d) which confers resistance to porphyrin-accumulating type herbicides in plant or algal cells when expressed therein, or a biologically functional equivalent thereof.

Another object of the present invention is to provide an isolated, purified DNA fragment having the following characteristics:

a) comprising a nucleotide sequence derived from a DNA fragment obtained from a strain of the unicellular green alga *Chlamydomonas reinhardtii* that exhibits resistance to porphyrin-accumulating type herbicides;

b) containing restriction sites for EcoRI, XhoI, PstI, PstI, PstI, PstI, PstI, BamHI, SalI, SalI, XhoI, HindIII, and KpnI, and having a restriction site map as shown in FIG. 1(*c*);

c) having a molecular size of approximately 10.0 kb; and d) which confers resistance to porphyrin-accumulating type herbicides in plant or algal cells when expressed therein, or a biologically functional equivalent thereof.

A further object of the present invention is to provide an isolated, purified DNA fragment having the following characteristics:

a) comprising a nucleotide sequence derived from a DNA fragment obtained from a strain of the unicellular green alga Chlamydomonas reinhardtii that exhibits resistance to porphyrin-accumulating type herbicides;

b) containing restriction sites for EcoRI, XhoI, PstI, PstI, PstI, PstI, PstI, BamHI, SalI, SalI, XhoI, HindIII, BamHI, SalI, HindIII, and KpnI, and having a restriction site map as shown in FIG. 1(d);

c) having a molecular size of approximately 13.8 kb; and d) which confers resistance to porphyrin-accumulating type herbicides in plant or algal cells when expressed therein, or a biologically functional equivalent thereof.

Further objects of the present invention are to provide plasmids and microorganisms containing any of the foregoing DNA fragments or biologically functional equivalents thereof, a method of conferring resistance to porphyrin-accumulating type herbicides upon plant or algal cells, comprising introducing said DNA fragments or biologically functional equivalents thereof into plant or algal cells in a functionally operable manner so that said DNA fragments or biologically functional equivalents thereof are expressed in said plant or algal cells, and the expression of the DNA fragment confers resistance to porphyrin-accumulating type herbicides upon the transformed plant or algal cells. It is preferred that cells cultured in vitro that have been transformed by the DNA fragments of the invention in a functionally operable manner are resistant to a porphyrin-accumulating type herbicide at a concentration of at least 0.01 $\mu$M, preferably at a concentration of at least 0.03 $\mu$M, most preferably at a concentration of at least 0.1 $\mu$M herbicide. When compound A or compound B are used as the test compounds, the range of concentration is preferably 0.01 to 0.3 $\mu$M, more preferably 0.03 to 0.6 $\mu$M, most preferably 0.1 to 0.3 $\mu$M. Otherwise the range is between 0.01 to 30 $\mu$M, more preferably 0.03 to 10 $\mu$M, most preferably 0.1 to 3 $\mu$M. The concentration of herbicide used to test resistance of transformed plants or tissues therefrom is to the high end of these ranges or even higher, and can be determined by the ordinarily skilled artisan by experimentation typical in the art. The herbicide used for testing herbicide resistance of cells in vitro or of whole transformed plants or algae is preferably a N-phenyl-tetrahydrophthalimide compound. N-(4-chloro-2-fluoro-5-propargyloxy)phenyl-3,4,5,6-tetrahydrophthalimide (compound A) or 7-fluoro-6-[(3,4,5,6,)-tetrahydrophthalimido]-4-(2-propynyl)-1,4-benzoxazin-3(2H)-one (referred to below as "compound B") are especially preferred for this purpose.

Another object of the present invention is to provide plants or algae into which have been introduced in a functionally operable manner said DNA fragments or biologically functional equivalents thereof.

A still further object of the present invention is to provide an isolated, purified genomic DNA fragment comprising the nucleotide sequence shown in SEQ ID NO:1; plasmids and microorganisms containing said DNA fragment; a method of conferring resistance to porphyrin-accumulating type herbicides upon plant or algal cells, comprising introducing the cDNA corresponding to the mRNA encoded by said DNA fragment that confers porphyric herbicide resistance on plant or algal cells, wherein said cDNA is expressed; and plants or algae into which cDNA corresponding to the mRNA encoded by said DNA fragment having the nucleotide sequence shown in SEQ ID NO:1 has been introduced, wherein said cDNA is expressed.

Yet further objects of the present invention include the use of any of the DNA fragments or biologically functional equivalents thereof disclosed herein as a genetic marker (for herbicide resistance), to produce a recombinant plasmid or transformed microorganism, to produce a probe useful in identifying related DNA sequences that confer resistance to porphyrin-accumulating type herbicides in plant and algal cells, and to produce plants or algae resistant to porphyrin-accumulating type herbicides.

The DNA fragments and biologically functional equivalents thereof of the present invention are hereinafter referred to as the "subject nucleic acid fragments" or "subject DNA fragments". Specific individual fragments will be designated by their restriction sites and molecular sizes (kb).

The present invention includes plasmids containing the above-mentioned DNA fragments or their biologically functional equivalents (hereinafter referred to as the "subject plasmids"), microorganisms containing these DNA fragments or their equivalents (hereinafter referred to as the "subject microorganisms"), plants or algae containing these DNA fragments or their equivalents (hereinafter referred to as the "subject plants"), and methods for conferring resistance to porphyrin-accumulating type herbicides upon plant and algal cells by using these DNA fragments or their equivalents.

With regard to the terminology used herein, the term "DNA fragments" refers not only to the subject DNA fragments, but also to degenerate isomers and genetically equivalent modified forms of these fragments. "Degenerate isomers" is taken here to mean isomers whose nucleotide base sequence is degenerately related to the original fragments; that is, all nucleic acid fragments including the corresponding mRNA or corresponding cDNA, that contain essentially the same genetic information as the original fragments. "Genetically equivalent modified forms" is taken here to mean DNA fragments that may have undergone base changes, additions, or deletions, but which essentially contain the same inherent genetic information as the original fragments.

Specific examples of the latter include DNA fragments whose nucleotide sequence shows high homology to the subject nucleic acid fragments, which are readily isolated using conventional DNA-DNA or DNA-RNA hybridization techniques, or that are amplified using known PCR (Polymerase Chain Reaction) methods, and which possess the ability to confer resistance to porphyrin-accumulating type herbicides when introduced by conventional transformation techniques into plant or algal cells normally sensitive to these herbicides.

The phrase "porphyrin-accumulating type herbicide" or the phrase "porphyric herbicides" refers to light-dependent herbicides, i.e., compounds that kill sensitive plants in the presence of light, but which exhibit no herbicidal activity in darkness, and which induce the accumulation of high levels of porphyrins in plants to which they have been applied. These herbicides include, for example, oxadiazon, flupropacil, [N-(4-chloro-2-fluoro-5-propargyloxy)phenyl-3,4,5,6-tetrahydrophtalimide (referred to below as compound A), the diphenyl ether herbicides such as acifluorfen, lactofen, oxyfluorfen, as well as the following: pentyl [2-chloro-5-(cyclohex-1-ene-1,2-dicarboximido)-4-fluorphenoxy]acetate, 7-fluoro-6-[(3,4,5,6,)-tetra-hydrophthalimido]-4-(2-propynyl)-1,4-benzoxazin-3(2H)-one (referred to below as "compound B"), 6-[(3,4,5,6-tetrahydro)pthalimido]-4-(2-propynyl)-1,4-benzoxazin-3 (2H)-one, 2-[7-fluoro-3-oxo-4-(2-propynyl)-3,4-dihydro-2H-1,4-benzoxazin- 6-yl]perhydroimidazo [1,5-a]pyridine-1,3-dione, 2-[(4-chloro-2-fluoro-5-propargyloxy)phenyl] perhydro-1-H-1,2,4-triazolo-[1,2-a]pyridazine-1,3-dione, 2-[7-fluoro-3-oxo-4-(2-propynyl)-3,4-dihydro-2H-1,4-benzoxazin-6-yl]5,6,7,8-1,2,4-triazolo[4,3-a]pyridine-3H-one, 2-[3-oxo-4-(2-propynyl)-3,4-dihydro-2H-1,4-benzoxazin-6-yl]-1-methyl-6-trifluoromethyl-2,4(1H,3H)-pyrimidinedione, 2-[6-fluoro-2-oxo-3-(2-propynyl)-2,3-dihydrobenzthiazol-5-yl]-3,4,5,6-tetrahydrophthalimide, 1-amino-2-[3-oxo-4-(2-propynyl)-3,4-dihydro-2H-1,4-benzoxazin-6-yl]-6-tri-fluoromethyl-2,4(1H,3H)-pyrimidinedione, as well as analogs of these compounds.

The subject nucleic acid fragments may be constructed by the artificial synthesis of their nucleotide sequences; however, they are more typically isolated from a mutant strain of the unicellular green alga *Chlamydomonas reinhardtii*, designated RS-3, that is resistant to porphyrin-accumulating type herbicides. Said mutant strain RS-3 is stored at the Chlamydomonas Genetics Center (address: DCMB Group, Department of Botany, Box 91000, Duke University, Durham, N.C., 27708-1000, USA) under the entry number CC-2674. Thus, the mutant strain RS-3 is publicly available for distribution. As will be described below, the microorganisms that host the plasmids containing the subject nucleic acid fragments are also on deposit under the terms of the Budapest Treaty, and are thus freely available as well. The plasmids hosted by these microorganisms can be readily extracted using conventional techniques and the subject fragments recovered by reference to the restriction maps shown in FIGS. 1(a)–1(d). It would be possible, for example, to introduce specific alterations into these fragments using PCR or other site-directed mutagenesis techniques, or to use the subject nucleic acid fragments or their corresponding cDNAs, PCR products, or oligonucleotides as probes to isolate other DNA fragments exhibiting high homology to the subject nucleic acid fragments, and thus to generate homologs as discussed above.

Further scope of the applicability of the present invention will become apparent from the detailed description and drawings provided below. It should be understood, however, that the following detailed description and specific examples, while indicating preferred embodiments of the invention, are given by way of illustration only since various changes and modifications within the spirit and scope of the invention will become apparent to those skilled in the art from this detailed description.

BRIEF DESCRIPTION OF THE DRAWINGS

The above and other objects, features, and advantages of the present invention will be better understood from the following detailed descriptions taken in conjunction with the accompanying drawings, all of which are given by way of illustration only and are not limitative of the present invention, in which:

FIG. 1(a): 3.4 kb DNA fragment designated as Xho3.4;

FIG. 1(b): 9.9 kb DNA fragment designated as Hind9.9;

FIG. 1(c): 10.0 kb DNA fragment designated as Hind10.0;

FIG. 1(d): 13.8 kb DNA fragment designated as Eco13.8;

FIGS. 1(c) and 2 show the PstI sites.

FIGS. 1(d) and 2 show the PstI sites.

DETAILED DESCRIPTION OF THE INVENTION

Figure 1:
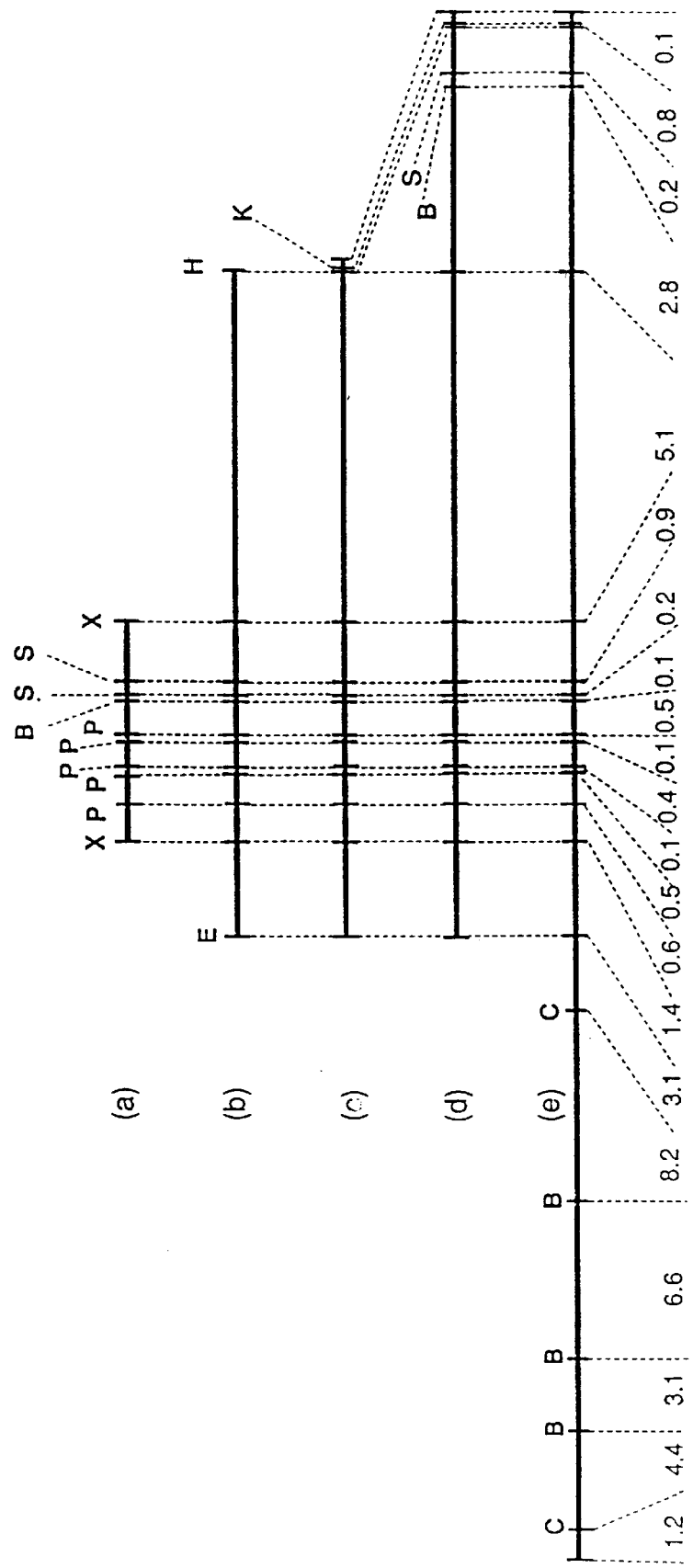
FIGS. 1(a)–1(d) shows restriction site maps of cloned DNA fragments of various sizes that confer resistance to porphyrin-accumulating type herbicides. The sizes of the fragments are indicated by the numbers (kb) in FIG. 1(e). Abbreviations: B, BamHI; S, SalI; P, PstI; X, XhoI; E, EcoRI; H, HindIII; K, KpnI; C, ClaI.
FIG. 1(e): approximately 40 kb DNA fragment harbored by cosmid clone 2955 (Cos2955).

The following detailed description of the invention is provided to aid those skilled in the art in practicing the present invention. Even so, the following detailed description should not be construed to unduly limit the present invention, as modifications and variations in the embodiments herein discussed may be made by those of ordinary skill in the art without departing from the spirit or scope of the present inventive discovery.

The contents of each of the references cited herein are herein incorporated by reference in their entirety.

OVERVIEW

The present nucleic acid fragments are obtained by conventional genetic engineering protocols as described in publications such as *Molecular Cloning*, 2nd Edition, by J. Sambrook, E. F. Frisch, and T. Maniatis, Cold Spring Harbor Publications (1989). Specifically, genomic DNA is extracted from the mutant strain RS-3 according to a protocol such as that described by E. H. Harris, *The Chlamydomonas Source Book*, pp. 610–613 (Chapter 12), Academic Press, San Diego (1989). Namely, *C. reinhardtii* cells are lysed and the DNA is extracted by treatment with a protease and surface active agents such as SDS or Sarkosyl. Genomic DNA is subsequently extracted by conventional techniques involving phenol-chloroform extraction, centrifugation, etc., to remove proteins, after which the DNA is recovered by ethanol precipitation. The DNA thus obtained can be further purified by sodium iodide-ethidium bromide density gradient centrifugation, and the lowermost, major band corresponding to nuclear genomic DNA recovered. Nuclear genomic DNA thus obtained is partially digested using an appropriate restriction enzyme such as Sau3AI. Linkers or adaptors are attached to both ends of the DNA fragments thus obtained using T4 DNA ligase. If necessary, excess free linkers or adaptors can be removed by gel filtration, and the fragments can then be inserted into an appropriate commercially available cosmid vector or a phage vector such as those derived from λ phage. Phage particles generated by in vitro packaging are transfected into *E. coli* and allowed to form colonies or plaques on solid media. A genomic DNA library can be obtained by isolating and maintaining individual *E. coli* clones harboring hybrid cosmids or by conventional methods for isolating and maintaining *E. coli* clones or phage particles in a mixture.

Since no porphyric herbicide resistance gene had been previously isolated and characterized from any plant or algal species prior to the present invention, it was not feasible to screen the genomic DNA library described above by synthesis of an oligonucleotide probe corresponding to the deduced nucleotide sequence of such a gene, labeling this probe with a radioisotope or fluorescent tag, and using this to select genomic DNA clones containing the subject DNA fragments. Therefore, the genomic clones containing subject DNA fragments were screened by transforming a strain of *Chlamydomonas reinhardtii* sensitive to porphyric herbicides with the genomic DNA from the cosmid library using normal transformation techniques for this organism (Kindle, K., *Proc. Natl. Acad. Sci. USA* Vol. 87, p. 1228 (1990); Boynton J. E. and Gillham, N. W., *Methods In Enzymology: Recombinant DNA, Part H*, R. Wu, Ed., Academic Press, San Diego, Calif., Vol. 217, p. 510, (1993)) to isolate hybrid cosmids containing nuclear genomic DNA fragments capable of conferring resistance to a porphyric herbicide. A restriction map of the hybrid cosmid clone thus obtained was determined, various restriction fragments were subcloned into the pBluescript vector, and subclones that conferred resistance to porphyric herbicides onto normally sensitive Chlamydomonas strains were selected. Using the subject DNA fragments and the subject plasmids as starting material, the nucleotide sequence of the 3.4 kb fragment was determined by the method of Sanger (Sanger, F. and Coulson, A. R. *J. Mol. Biol.*, Vol. 94, p. 441 (1975); Sanger, F., Nicklen, and Coulson, A. R. *Proc. Natl. Acad. Sci. USA*, Vol. 74, p. 5463 (1977)) or improved versions of this method. Sequences of the larger 9.9, 10.0, and 13.8 kb fragments or the cDNAs corresponding to these fragments can be determined by the same methodology. The transcriptional initiation site of the porphyric herbicide resistance gene can be localized in one or more of these overlapping fragments using the primer extension technique described by Bina-Stem, M. et al. (*Proc. Natl. Acad. Sci. USA*, Vol. 76, p. 731, (1977)) and Sollner-Webb and Reeder, R. H. (*Cell*, Vol. 18, p. 485 (1978)), or by the S1 mapping technique described by Berk, A. J. and Sharp, P. A. (*Proc. Natl. Acad. Sci. USA*, Vol. 75, p. 1274 (1978)). Typically, promoter sequences that are responsible for the regulation of gene expression are found in a region approximately 1 kb to 10 kb upstream of the transcription initiation site. The promoter region of the gene which confers resistance to porphyric herbicides can be determined by using standard Chlamydomonas transformation techniques (Kindle, K., *Proc. Natl. Acad. Sci. USA*, Vol. 87, p. 1228 (1990)) and chimeric reporter constructs. For example, various lengths of the region upstream of the transcription start site can be joined to an appropriate heterologous reporter gene such as GUS or one encoding enzymatically-determined antibiotic resistance. By introducing these constructs into *Chlamydomonas reinhardtii* using transformation and monitoring reporter gene expression, the promoter region of the gene conferring resistance to porphyric herbicides can ultimately be determined. In addition, a transcription terminator sequence is expected to be present within one or more of the overlapping cloned genomic DNA fragments downstream of the poly-A addition signal found in the 3' non-coding region downstream of the stop codon.

Herbicide-resistant transformants were obtained from the 13.8 and 10.0 kb fragments from RS-3 at about 80-fold higher frequency than from the 3.4 kb fragment. This is consistent with the 13.8 and 10.0 kb fragments containing the entire coding sequence plus upstream and downstream regulatory elements and integrating non-homologously and randomly in the nuclear genome of the herbicide-sensitive recipient strain. In contrast, the low transformation frequency observed with the 3.4 kb fragment is consistent with this fragment containing only a portion of the RS-3 gene which must integrate into the herbicide-sensitive RS-3 gene of the recipient by homologous recombination to be expressed. Nuclear transformants of *Chlamydomonas reinhardtii* arise much more frequently by random non-homologous recombination than by homologous recombination as has been demonstrated by experiments with the nuclear nit-1 gene by Sodeinde, O. A. and Kindle, K. L., (*Proc. Natl. Acad. Sci. USA* Vol. 90, p.9199 (1993)).

The foregoing will be described in detail in the Examples presented below, although the present invention is not limited to these Examples.

EXAMPLE 1

Construction of *Chlamydomonas reinhardtii* Genomic DNA Library

The porphyric herbicide-resistant mutant strain RS-3 of the unicellular alga *Chlamydomonas reinhardtii* (Chlamydomonas Genetics Center, strain GB-2674) was cultured mixotrophically under 200 $\mu E/m^2/sec$ photosynthetically active radiation with shaking for 5 days in TAP liquid medium composed of 7 mM $NH_4Cl$, 0.4 mM $MgSO_4 \cdot 7H_2O$, 0.34 mM $CaCl_2 \cdot 2H_2O$, 25 mM potassium phosphate, 0.5 mM Tris (pH 7.0), 1 ml/L Hutner trace elements, and 1 ml/L glacial acetic acid (Harris, E. H., *The Chlamydomonas Sourcebook*, Academic Press, San Diego, 1989, pp. 576–77) also containing 0.03 $\mu M$ compound A. Six liters of culture containing cells in early stationary growth phase ($7.6 \times 10^6$ cells/ml) were harvested. Cells were collected by centrifugation (8,000×g, 10 min, 4° C.), resuspended in 50 ml of TEN buffer composed of 10 mM Tris-HCl, 10 mM EDTA, 150 mM NaCl, pH 8.0, recentrifuged, and resuspended again in 50 ml of TEN buffer. To this were gently added 5 ml of 20% (w/v) SDS, 5 ml of 20% Sarkosyl, and 4 ml of protease solution composed of 5 g of protease (Boehringer Mannheim No. 165921), 10 ml of 1M Tris-HCl (pH 7.5), and 0.11 g of $CaCl_2$ in a total volume of 100 ml of deionized distilled water. This was mixed by slowly rotating the solution in a bottle for 24 hr at 4° C. Sixty ml of phenol-CIA (phenol pre-saturated with TEN buffer and mixed well with an equal volume of a chloroform:isoamyl-alcohol, 24:1, v/v) were subsequently added, and the contents were rotated in the same bottle at room temperature for 1 hr.

The contents were then separated by centrifugation (15,000×g, 20 min, room temperature), the aqueous (upper) phase was recovered and mixed with 2 volumes of 95% (v/v) ethanol gently but thoroughly, and the DNA precipitated by placing the contents at −20° C. overnight. The resulting precipitate was recovered by centrifugation (1,500×g, 20 min, 4° C.) and washed once with ice-cold 70% (v/v) ethanol. Excess ethanol was removed and the DNA precipitate was dried under nitrogen flow for 5 min at room temperature.

The dried precipitate was subsequently dissolved in 60 ml of 10 mM Tris (pH 7.5), and under dim light, the following were added: 8 ml of 10-fold concentrated TEN buffer, 0.4 ml of ethidium bromide solution (10 mg/ml), 9.8 ml of 10 mM Tris-HCl (pH 7.5), and 120 ml of sodium iodide (NaI)-saturated TEN buffer. The contents were mixed by gently inverting the container and 25 ml were dispensed into each of 8 centrifuge tubes. These were subjected to ultracentrifugation in a Beckman 70 Ti rotor (44,000 rpm, 40 hr, 20° C.). After ultra-centrifugation, the lowermost, major band consisting of nuclear DNA was visualized by long-wave UV illumination, and recovered by use of a large-gauge syringe. The DNA in this band was again subjected to ultracentrifugation in a Beckman 70 Ti rotor (44,000 rpm, 44 hr, 20° C.). The purified nuclear DNA band was recovered as above.

Ethidium bromide was extracted from the solution containing the recovered nuclear DNA by adding isoamyl alcohol saturated with 1–2 volumes of TEN buffer and subsequently discarding the alcohol (upper) phase. After repeating this step three times, the nuclear DNA from which ethidium bromide had been removed was precipitated by the addition of 2.5 volumes of ice-cold ethanol. The precipitate recovered was washed twice in ice-cold 95% (v/v) ethanol, redissolved in a small volume of 10 mM Tris-HCl (pH 7.5), and stored at −20° C. An aliquot of this sample was diluted 100-fold and the concentration and purity of the DNA were quantified by measuring the absorbance at 260 nm and 280 nm.

Twenty five μg of the genomic DNA thus obtained were partially digested by reaction with 0.83 units of the restriction enzyme Sau3AI at 37° C. for 15 min in 277 μl of 10 mM Tris-HCl buffer (pH 7.5) containing 50 mM NaCl, 10 mM MgCl$_2$, and 1 mM dithiothreitol. The reaction mixture was extracted with an equal volume of phenol equilibrated with Tris buffer (pH 7.5) followed by an equal volume of chloroform. Three M ammonium acetate was added to give a final concentration of 0.4M, followed by the addition of 2 volumes of ice-cold ethanol. This solution was mixed thoroughly and a DNA precipitate formed following storage of the sample overnight at −20° C. The precipitate was recovered by centrifugation in a tabletop centrifuge (10,000 rpm, 10 min), washed in 70% (v/v) ethanol and re-centrifuged. The precipitate was then resuspended in 20 μl TE buffer (composed of 10 mM Tris-HCl, 0.1 mM EDTA .2Na), and the DNA was dephosphorylated by the addition of 70 μl of deionized distilled water, 10 μl of 10-fold concentrated CIAP buffer composed of 0.5M Tris-HCl (pH 8.5) and 1 mM EDTA, and 1 unit of CIAP (Calf Intestinal Alkaline Phosphatase). The total volume of 100 μl was incubated for 60 min at 37° C. and the reaction halted by the addition of 3 μl of 0.5M EDTA (pH 8.0) and heat-treatment for 10 min at 68° C. The DNA was subjected to phenol and chloroform extractions and precipitated by the addition of ethanol containing ammonium acetate as described above.

The precipitate was washed with 70% (v/v) ethanol and the recovered DNA redissolved in TE buffer to a final concentration of 0.5 μg/ml. Subsequently, the commercially available cosmid vector SuperCos-1 (Stratagene Inc.) was prepared following the protocol outlined in the SuperCos-1 instruction manual provided by the manufacturer. The vector was digested with the restriction enzyme XbaI, dephosphorylated with CIAP, re-digested with the restriction enzyme BamHI, recovered by ethanol precipitation, and redissolved in TE buffer to a final concentration of 1 μg/ml. Two point five μg of the prepared genomic DNA fragments were ligated to 1 μg of the prepared SuperCos-1 vector in 20 μl of reaction buffer (composed of 1 mM ATP, 50 mM Tris-HCl (pH7.5), 7 mM MgCl$_2$, and 1 mM dithiothreitol) by the addition of 2 units of T4 DNA ligase and incubation at 4° C. overnight. Point five μg of the hybrid cosmids thus generated were then packaged into λ phage particles capable of infecting E. coli by the use of a commercial in vitro phage packaging kit (Gigapack II XL, Stratagene Inc.) following the protocol outlined in the instruction manual provided. λ phage particles harboring these hybrid cosmids were then transfected into the E. coli strain NM554 (Stratagene, Inc.) by the procedure described below, and these E. coli cells were allowed to form colonies on LB medium plates (10 g/L NaCl, 10 g/L Bacto-tryptone, 5 g/L yeast extract, pH 7.5, 1.5% (w/v) agar) containing 50 μg/ml ampicillin. The transfection protocol is as follows: (1) a single colony of E. coli strain NM554 was inoculated into 50 ml of medium (5 g/L NaCl, 10 g/L Bacto-tryptone, pH 7.4, 0.2% (w/v) maltose, 10 mM MgSO$_4$) and cultured by shaking vigorously overnight at 37° C.; (2) cells were collected by centrifugation (4,000 rpm, 10 min, 4° C.) and resuspended in 10 mM MgSO$_4$ to an OD$_{600}$ of 0.5; (3) 25 μl of this bacterial suspension were mixed with 25 μl of a ½oth dilution of the phage particle solution harboring hybrid cosmids prepared as described above. The phage were infected into E. coli by allowing the mixture to stand at room temperature for 30 min. Two hundred μl of LB medium (10 g/L NaCl, 10 g/L Tryptone, 5 g/L yeast extract) were subsequently added and the suspension was incubated at 37° C. for 1 hr to allow for the expression of ampicillin resistance. The suspension was then plated onto LB medium plates containing 50 μg/ml ampicillin and colonies formed following incubation at 37° C. overnight. The transformation efficiency of the ampicillin marker was $1.7 \pm 0.1 \times 10^5$ transformants/μg DNA. The E. coli colonies ontaining hybrid cosmids thus obtained were individually picked with sterile toothpicks and transferred into microtiter plate wells (Falcon, 24-well) each containing 0.5 ml of LB medium containing 50 μg/ml ampicillin and incubated without shaking at 37° C. for 24 hr. Ten thousand and eighty individual clones were thereby isolated in 420 microtiter plates. Then, 187.5 μl of medium were removed from each well and combined in pools of 8 clones each (1.5 ml total) into 1,260 microtubes. The bacteria in each microtube were pelleted by centrifugation (10,000 rpm, 5 min, room temperature) and subjected to DNA extraction. The bacteria remaining in the microtiter plates were frozen at −70° C. following the addition of an equal volume of 30% (w/v) glycerol. These plates were subsequently stored at −20° C.

EXAMPLE 2

Screening of the Genomic DNA Library

The various experimental methods used to screen the genomic DNA library are described below (methods A, B, and C).

A. DNA Extraction

Extraction of cosmid DNA from E. coli harboring the genomic DNA library generated as described in Example 1, as well as extraction of the plasmid pARG7.8 (Debuchy, R., Purton, S., Rochaix, R. D., EMBO J., vol. 8, p. 2803, (1989)), utilized as a transformation control, was performed by standard extraction methods (for example, J. Sambrook, E. F. Frisch, T. Maniatis, Molecular Cloning, 2nd edition, Cold Spring Harbor Publications, (1989), Vol. I, pp. 1.38–1.39). A description of the specific protocol follows.

The bacterial pellet in each microtube was thoroughly suspended in 100 μl of Solution I (composed of 50 mM glucose, 25 mM Tris-HCl (pH8.0), 10 mM EDTA), to which 200 μl of Solution II (composed of 0.2N NaOH, 1% (w/v) SDS) were added. Each microtube was capped, the contents were gently mixed by inverting the tube 5–6 times, and the tube was cooled by placing on ice. One hundred and fifty μl of ice-cold Solution III (composed of 60 ml of 5M potassium acetate (pH 4.8), 11.5 ml of glacial acetic acid, and 28.5 ml of deionized, distilled water) were subsequently added, the contents were mixed well, and the tubes cooled on ice for 5 min. The tubes were then centrifuged in a tabletop centrifuge (10,000 rpm, 2 min, 4° C.) and the supernatant recovered. An equal volume of phenol:chloroform (1:1, v/v, pH 7.5)

was added to the recovered supernatant, the contents were thoroughly mixed by vortexing, and the tubes were again centrifuged in a tabletop centrifuge (10,000 rpm, 2 min, 4° C.), and the supernatant recovered. After re-extracting with chloroform, 900 μl of ethanol were added to the supernatant and mixed. The DNA was precipitated by cooling the tubes on ice and the precipitates were recovered by centrifugation in a tabletop centrifuge (12,000×g, 2 min, 4° C.). The precipitates were washed in 70% (w/v)ethanol and recovered again by centrifugation (12,000×g, 2 min, 4° C.). Excess ethanol was removed by opening the microtube caps and allowing the ethanol to evaporate at room temperature for 10 min. The precipitates thus recovered were redissolved in 50 μl of TE buffer (composed of 10 mM Tris-HCl (pH 7.5), 0.1 mM EDTA-2Na) to solubilize the DNA.

B. Transformation by the Glass Bead Method

The glass bead transformation protocol, when employed, followed that described by Kindle, K. (*Proc. Natl. Acad. Sci USA*, vol. 87, p. 1228, (1990)). The actual protocol employed is presented below.

First, the unicellular green alga *Chlamydomonas reinhardtii* strain CC-425 (arginine auxotroph arg-2, cell wall deficient cw-15) was cultured mixotrophically for 2 days to a cell density of 1–2×10$^6$ cells/ml in TAP liquid medium composed of 7 mM NH$_4$Cl, 0.4 mM MgSO$_4$.7H$_2$O, 0.34 mM CaCl$_2$.2H$_2$O, 25 mM potassium phosphate-0.5 mM Tris (pH 7.0), 1 ml/L Hutner trace elements, 1 ml/L glacial acetic acid (described in Harris, E. H., *The Chlamydomonas Sourcebook*, Academic Press, San Diego, 1989, pp. 576–77)+50 μg/ml arginine. Cells were collected by centrifugation of the culture (8,000×g, 10 min, 20° C.) and resuspended in a small volume of TAP to give a final density of 2.8×10$^8$ cells/ml.

In a small sterile test tube containing 0.3 gram of sterile glass beads (0.45–0.52 mm), 0.3 ml of this cell suspension, 0.5–1.0 μg of plasmid or 1–2 μg of library DNA, and 0.1 ml of 20% (w/v) polyethylene-glycol (PEG) were added, mixed gently, then vortexed at high speed for 15 seconds using a vortex mixer. The tube was allowed to sit for 2 min and then vortexed for another 15 sec in the same manner.

The cell suspension was then plated, 0.2 ml per plate, onto 2 plates of solid medium (composition: a) when using the arginine auxotroph as a transformation marker: TAP medium+1.5% (w/v) agar; or b) when using resistance to porphyric herbicides as a transformation marker: TAP medium+0.1μM compound A+50 μg/μl arginine+1.5% (w/v) agar) and allowed to form colonies under illumination.

C. Transformation by the Particle Gun Method

The particle gun transformation protocol, when employed, followed that described by Boynton, J. E. & Gillham, N. W. (*Methods in Enzymol.: Recombinant DNA, Part H*, Wu, R. ed., Academic Press, San Diego, Calif., 1993, vol. 217, p. 510). The actual protocol employed is described below.

First, the unicellular green alga *Chlamydomonas reinhardtii* strain CC-48 (arginine auxotroph arg-2) was cultured mixtrophically for 2 days in TAP liquid medium composed of 7 mM NH$_4$Cl, 0.4 mM MgSO$_4$.7H$_2$O, 0.34 mM CaCl$_2$.2H$_2$O, 25 niM potassium phosphate—0.5 mM Tris (pH 7.0), 1 ml/L Hutner trace elements, 1 ml/L glacial acetic acid (described in Harris, E. H., *The Chlamvdomonas Sourcebook*, Academic Press, San Diego, 1989)+50 μg/μl arginine to a cell density of 1.5–3×10$^6$ cells/ml. Cells were collected by centrifugation of the culture (8,000×g, 10 min, 20° C.) and resuspended in a small volume of HS medium (composed of 500 mg/L NH$_4$Cl, 20 mg/L MgSO$_4$.7H$_2$O, 10 mg/L CaCl$_2$.2H$_2$O, 1,440 mg/L K$_2$HPO$_4$, 720 mg/L K$_2$HPO4, 1.2 g/L anhydrous sodium acetate, 1 ml/L Hutner trace elements (described in Harris, E. H., *The Chlamydomonas Sourcebook*, Academic Press, San Diego, 1989) to a cell density of 1.14 ×10$^8$ cells/ml. One ml of this cell suspension was added to small test tubes already containing 1 ml of HS medium+0.2% agar (Difco Bacto Agar) pre-warmed to 42° C. After gentle mixing, 0.7 ml of the suspension was plated onto each of two plates of HSHA agar (composed of 500 mg/L NH$_4$Cl, 20 mg/L MgSO$_4$.7H$_2$O, 10 mg/L CaCl$_2$.2H$_2$O, 1,440 mg/L K$_2$HPO$_4$, 720 mg/L K$_2$HPO$_4$, 2.4 g/L anhydrous sodium acetate, and 1 ml/L Hutner trace elements (described in Harris, E. H., *The Chlamydomonas Sourcebook*, Academic Press, San Diego, 1989) also containing 50 μg/μl ampicillin, and the cells were affixed to the surface of the plates by drying them in the dark.

Next, 60 mg of gold particles (1 μm diameter, DuPont Biotechnology Systems, 7556, Wilmington, Del.) and 1 ml of ethanol were added to a microtube and vortexed at the highest speed for 2 min using a vortex mixer. The gold particles were subsequently recovered by centrifugation (10,000 rpm, 1 min, room temperature), and this washing procedure was repeated 3 times. The recovered gold particles were subsequently resuspended in 1 ml of sterile distilled water. The particles were again recovered by the same centrifugation procedure, and this washing procedure was repeated another 2 times. Finally, the gold particles were resuspended in 1 ml of sterile distilled water. Fifty μl of this particle suspension were added to a microtube, to which 5 μl of DNA (1 μg/μl), 50μl of 2.5M CaCl$_2$, and 20 μl of 0.1M spermidine were added while agitating with a vortex mixer. Mixing was continued for 3 min after which the precipitate was recovered by centrifugation (10,000 rpm, 10 min, room temperature). The precipitated gold particles were resuspended in 250 μl ethanol, recovered again by the same centrifugation procedure, and finally resuspended in 60 μl ethanol. Chlamydomonas cells prepared as described above were bombarded with the DNA-coated gold particles thus obtained using a particle gun. Immediately afterwards, the cells were recovered from the surface of the agar plates into 1.5 ml of HS liquid medium by scraping gently with a glass rod. Half of this suspension was spread onto each of two selective agar media plates (composition: a) when using the arginine auxotroph as a transformation marker: TAP medium+1.5% (w/v) agar; b) when using resistance to porphyrin-accumulating type herbicides as a transformation marker: TAP medium+0.3 μM compound A+50 μg/μl arginine+1.5% (w/v) agar) and allowed to form colonies under illumination (75–90 μMolm$^{-2}$sec$^{-1}$).

The experimental methods described above were used to screen the genomic DNA library. Details of the screening procedures are presented below as separate primary, secondary, and tertiary screening steps.

1. Primary Screening

The recipient unicellular green alga *Chlamydomonas reinhardtii* strain CC-425 (arginine auxotroph arg-2, cell wall deficient cw-15) was transformed with pARG 7.8 (plasmid DNA) together with the library DNA (a mixture of DNAs extracted from 48 clones) using the glass bead method (see above for details). Half of the cells in each transformation experiment (3.0×10$^7$ cells) were used to determine the transformation frequency as indicated by the arginine prototroph phenotype. The remaining half (3.0×10$^7$ cells) were examined for acquired resistance to porphyric herbicide. This experiment was repeated 198 times, and in total, 9,504 individual clones of the library were screened. In total, 7,046 arginine prototrophs were obtained from 5.8×

$10^9$ cells screened. Assuming all these arginine prototroph colonies are true transformants, the transformation frequency averaged $1.2 \times 10^{-6}$. Additionally, one clone was obtained that exhibited resistance to porphyric herbicide (i.e., that grew in the presence of compound A) from $5.8 \times 10^9$ cells screened. This colony was also able to grow normally on media lacking arginine, and exhibited a loss of motility when cultured in liquid media.

The DNA pool of 48 clones containing the cosmid which had given rise to the colony exhibiting resistance to porphyric herbicide (cosmid clone 2953-3000) is referred to as Cos2953-Cos3000.

2. Secondary Screening

The recipient unicellular green alga *Chlamydomonas reinhardtii* strain CC-48 (arginine auxotroph arg-2) was transformed with the DNAs shown in Table 1 by the particle gun method (see above for details). The results are also shown in Table 1.

Transformation with the DNA pool containing the 24 clones Cos2953–Cos2976 gave rise to colonies resistant to compound A, thus indicating that the porphyrin-accumulating type herbicide resistance gene must be contained within this pool.

TABLE 1

| Sample DNA | No. of colonies exhibiting arginine prototrophy | No. colonies exhibiting resistance to herbicide (per $10^8$ cells) |
|---|---|---|
| no DNA | 0 | 0 |
| pARG 7.8 | 165 | 0 |
| pARG 7.8 + Cos2953–Cos3000 | 46 | 4 |
| pARG 7.8 + Cos2953–Cos2976 | 67 | 20 |
| pARG 7.8 + Cos2977–Cos3000 | 40 | 0 |
| pARG 7.8 + Cos5833–Cos5856 | 29 | 0 |
| pARG 7.8 + Cos1033–Cos1056 | 34 | 0 |

3. Tertiary Screening

The recipient unicellular green alga *Chlamydomonas reinhardtii* strain CC-48 (arginine auxotroph arg-2) was transformed with hybrid cosmid DNA prepared as described from the respective clones which make up the DNA pool Cos2953–Cos2976 by the particle gun method (see above for details). These results are shown in Table 2. Transformation only with the hybrid cosmid contained within clone Cos2955 gave rise to colonies resistant to compound A.

TABLE 2

| Cosmid clone No. | No. of colonies exhibiting resistance to herbicide (per $1.6 \times 10^8$ cells) | Cosmid clone No. | No. of colonies exhibiting resistance to herbicide (per $1.6 \times 10^8$ cells) |
|---|---|---|---|
| No DNA | 0 | 2965 | 0 |
| 2953 | 0 | 2966 | 0 |
| 2954 | 0 | 2967 | 0 |
| 2955 | 28 | 2968 | 0 |
| 2956 | 0 | 2969 | 0 |
| 2957 | 0 | 2970 | 0 |
| 2958 | 0 | 2971 | 0 |
| 2959 | 0 | 2972 | 0 |
| 2960 | 0 | 2973 | 0 |
| 2961 | 0 | 2974 | 0 |
| 2962 | 0 | 2975 | 0 |
| 2963 | 0 | 2976 | 0 |
| 2964 | 0 | | |

In order to confirm this result, purified hybrid cosmid DNA from Cos2955 was prepared using either a minicolumn plasmid purification method (Quiagen Inc.) or the cesium chloride density gradient centrifugation method, and the transformation experiments were repeated using the same protocol described above. These results are shown in Table 3. Transformation with Cos2955 DNA reproducibly gave rise to numerous colonies exhibiting resistance to compound A, indicating that a porphyric herbicide resistance gene must be contained within this hybrid cosmid DNA.

TABLE 3

| Cosmid clone No. | No. of colonies exhibiting resistance to herbicide (per $2.4 \times 10^8$ cells) |
|---|---|
| No DNA | 0 |
| 2955 (column-purified) | 91 |
| SuperCos-1 vector | 0 |
| 2955 (CsCl purified) | 264 |

EXAMPLE 3

Construction of Restriction Map and Subcloning

Hybrid cosmid DNA from clone Cos2955 was purified by the CsCl density gradient centrifugation method. The purified hybrid cosmid DNA (referred to below as Cos2955 DNA), or its subclone isolated as described below, was digested with the restriction enzymes EcoRI, SalI, BamHI, ClaI, KpnI, XhoI, PstI, and HindIII either alone or in combination, and the sizes of the fragments thus generated were estimated by 0.8% agarose gel electrophoresis (25 V, 15 hr). From an analysis of the sizes of each fragment in single and double digests, a restriction map was constructed. This result is shown in FIG. 1(e). PstI sites were determined in the 3.4 kb DNA fragment shown in FIG. 1(a). Cos2955 DNA contains sites for the following restriction enzymes (in order and with the distances (kB) between sites given in parentheses): ClaI (4.4) BamHI (3.1) BamHI (6.6) BamHI (8.2) ClaI (3.1) EcoRI (1.4) XhoI (0.6) PstI (0.5) PstI (0.1) PstI (0.4) PstI (0.1) PstI (0.5) BamHI (0.1) SalI (0.2) SalI (0.9) XhoI (5.1) HindIII (2.8) BamHI (0.2) SalI (0.8) and HindIII. The total molecular size (nucleic acid length) of the nuclear DNA fragment in Cos2955 conferring resistance to porphyrin-accumulating type herbicides is approximately 40.4 kb.

Cos2955 and the commercially-available plasmid pBluescript-II KS+ (pBS, Stratagene, Inc.) were cut with individual restriction enzymes or an appropriate combination of two restriction enzymes, extracted with phenol/chloroform, and the DNA fragments were recovered by ethanol precipitation. The pBS vector was dephosphorylated by treatment with CIAP if necessary and the pBS vector and the digested Cosmid 2955 DNA fragments were ligated using T4 DNA ligase. The hybrid plasmids thus obtained were introduced into the *E. coli* strain XL1-Blue by electroporation (12.5 kV/cm, 4.5 ms) and spread onto LB agar plates (composed of 10 g/L NaCl, 10 g/L Tryptone, 5 g/L yeast extract, 1.5% (w/v) agar and also containing 1 mM IPTG and 50 µg/ml ampicillin) upon which 2% (w/v) X-gal had been spread. From these, white colonies were isolated, i.e., those clones that had taken up the pBS vector and were thus ampicillin-resistant, which had a DNA fragment derived from Cos2955 DNA inserted into the cloning site of the pBS vector and were thus white in color. The isolated colonies were cultured in the presence of ampicillin, and plasmid DNA was subsequently isolated from these colonies by the alkaline lysis method (J. Sambrook, E. F. Frisch, T. Maniatis, *Molecular Cloning*, 2nd edition, Cold Spring Harbor, Publications, (1989), Vol. I, pp. 1.38–1.39). The isolated plasmids were re-digested with the restriction enzyme(s) used for cloning to release the inserts, and the sizes of the inserted fragments obtained were again estimated by 0.8% (w/v) agarose gel (75 V, 5 hr) electrophoresis. When an insert of the desired size was obtained, it was subjected to further restriction analysis in order to confirm that the correct DNA fragment had been cloned. The DNA fragments thus cloned are shown in FIGS. 1(a)–1(d). In order to identify the clone containing the porphyric herbicide resistance mutation rs-3, the recipient *Chlamydomonas reinhardtii* strain CC-48 (arginine auxotroph arg-2) was transformed with DNA from the pBS subclones of Cos2955 by the particle gun method (see above for details). The pBS subclones of Cos2955 that were able to confer resistance to compound A contained the Eco13.8, Hind10.0, and Xho3.4 fragments. These results confirmed that these DNA fragments contain the porphyric herbicide resistance mutation rs-3.

Herbicide-resistant transformants were obtained from the 13.8 and 10.0 kb fragments from RS-3 at about 80-fold higher frequency than from the 3.4 kb fragment (Table 4). This is consistent with the 13.8 and 10.0 kb fragments containing the entire coding sequence plus upstream and downstream regulatory elements, and integrating non-homologously and randomly in the nuclear genome of the herbicide-sensitive recipient strain. In contrast, the low transformation frequency observed with the 3.4 kb fragment is consistent with this fragment containing only a portion of the RS-3 gene which must integrate into the herbicide-sensitive RS-3 gene of the recipient by homologous recombination to be expressed. Nuclear transformants of *Chlamydomonas reinhardtii* arise much more frequently by random non-homologous recombination than by homologous recombination, as has been demonstrated for the nuclear nit-1 gene by Sodeinde, O. A. and Kindle, K. L. (*Proc. Natl. Acad. Sci. USA* vol. 90, p. 9199 (1993)).

TABLE 4

| pBS insert | No. of colonies exhibiting resistance to herbicide (per 2.4 × 10$^8$ cells) |
| --- | --- |
| No DNA | 0 |
| Eco13.8 or Hind10.0 | 894 |
| Xho3.4 | 10 |

Eco13.8 is a DNA fragment of approximately 13.8 kb that is able to confer resistance to porphyric herbicides, and which contains sites for the following restriction enzymes (in order and with the distance (Kb) between sites given in parentheses; this same notation will be used throughout): EcoRI (1.4) XhoI (0.6) PstI (0.5) PstI (0.1) PstI (0.4) PstI (0.1) PstI (0.5) BamHI (0.1) SalI (0.2) SalI (0.9) XhoI (5.1) HindIII (2.8) BamHI (0.2) SalI (0.8) and HindIII (0.1>) KpnI. The restriction site map for this fragment is shown in FIG. 1(d). Hind10.0 is a DNA fragment of approximately 10.0 kb that is able to confer resistance to porphyric herbicides, and which contains sites for the following restriction enzymes: EcoRI (1.4) XhoI (0.6) PstI (0.5) PstI (0.1) PstI (0.4) PstI (0.1) PstI (0.5) BamHI (0.1) SalI (0.2) SalI (0.9) XhoI (5.1) HindIII (0.1>) KpnI. Its restriction site map is shown in FIG. 1(c). Furthermore, the Hind10.0 fragment is a derivative of the Eco13.8 fragment listed above from which has been deleted a DNA fragment of approximately 3.8 kB containing sites for the restriction enzymes HindIII (2.8) BamHI (0.2) SalI (0.8) HindIII. Hind9.9 (FIG. 1(b)) is derived from Hind10.0 by deletion of an approximately 0.1 kB fragment (see FIGS. 1(b) and 1(c)). Xho3.4 is a DNA fragment of approximately 3.4 kB that is able to confer resistance to porphyric herbicides, and which contains sites for the restriction enzymes XhoI (0.6) PstI (0.5) PstI (0.1) PstI (0.4) PstI (0.1) PstI (0.5) BamHI (0.1) SalI (0.2) SalI (0.9) XhoI. Its restriction site map is shown in FIG. 1(a). Xho3.4 is a derivative of Eco13.8, described above, from which has been deleted a DNA fragment of approximately 9.1 kB containing sites for the restriction enzymes XhoI (5.1) HindIII (2.8) BamHI (0.2) SalI (0.8) HindIII (0.1>) KpnI and a DNA fragment of approximately 1.4 kB containing sites for the restriction enzymes EcoRI (1.4) XhoI.

Figure 2:
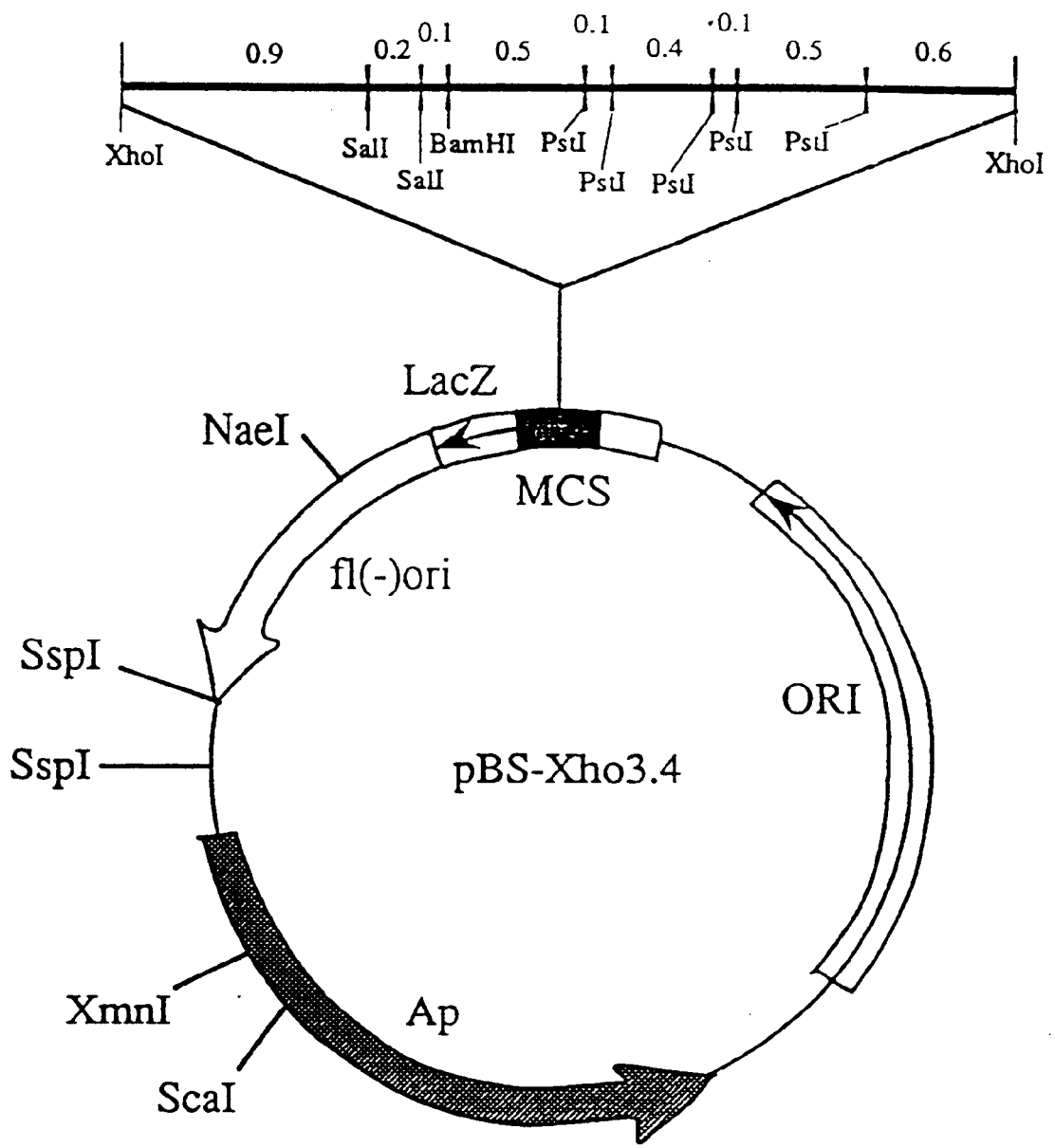
FIG. 2 shows the structure of a pBS plasmid containing an Xho3.4 fragment insert. Distances between restriction sites (kb) are shown by the numbers in the insert.
Figure 3:
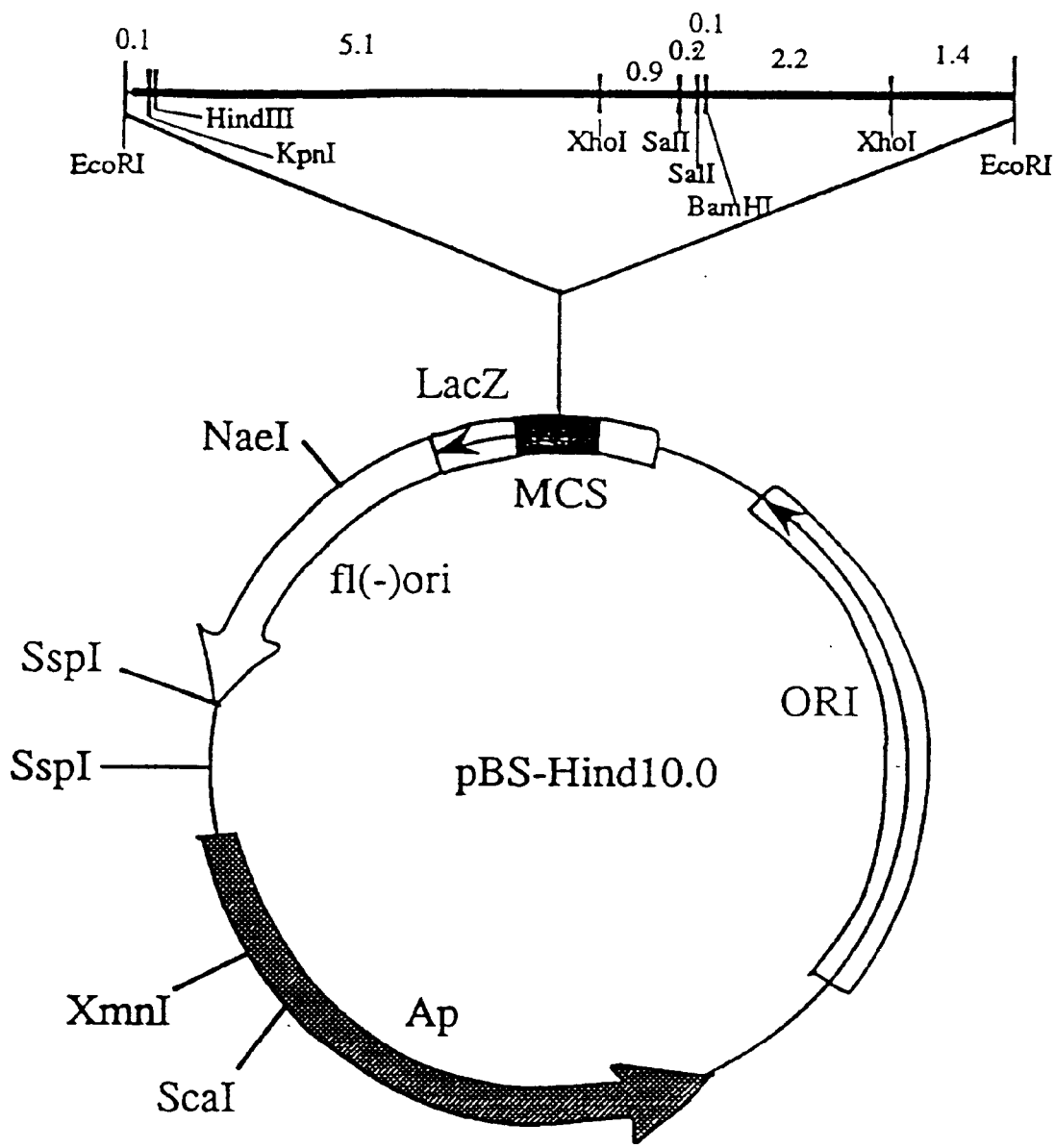
FIG. 3 shows the structure of a pBS plasmid containing a Hind10.0 fragment insert. Distances between restriction sites (kb) are shown by the numbers in the insert.
Figure 4:
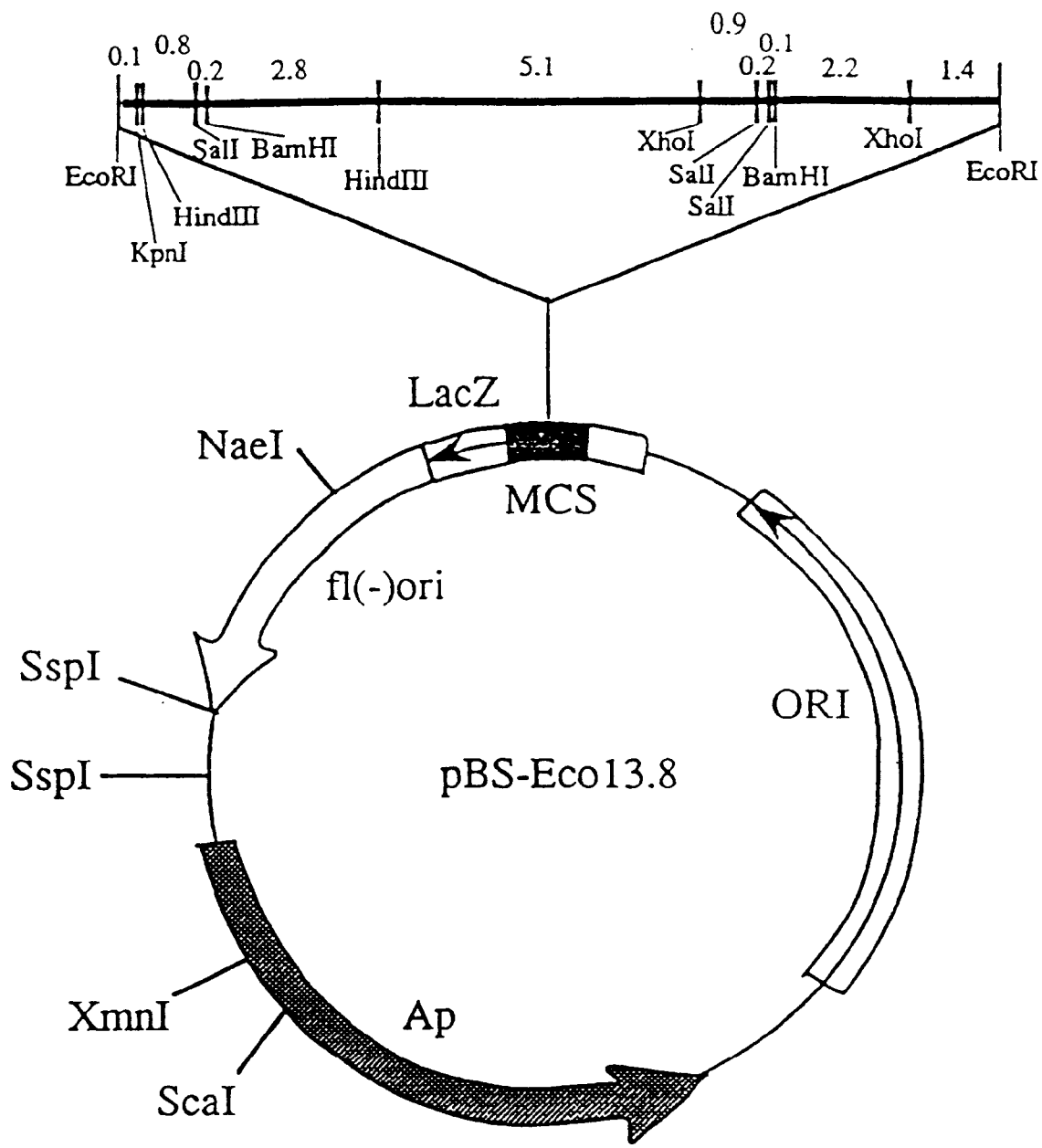
FIG. 4 shows the structure of a pBS plasmid containing an Eco13.8 fragment insert. Distances between restriction sites (kb) are shown by the numbers in the insert.

*E. coli* strains containing pBS plasmids with the fragments described above inserted, i.e., Eco13.8, Hind10.0, and Xho3.4 (FIGS. 2–4) have been deposited with the Chlamydomonas Genetics Center, c/o Dr. Elizabeth H. Harris, DCMB Group, LSRC. Building, Research Drive, Box 91000, Duke University, Durham, N.C., 27708-1000. These deposits are designated P-563, P-564, and P-566, respectively. *E. coli* containing Cos2955 has also been deposited with the Chlamydomonas Genetics Center under the designation P-561. In addition, *Escherichia coli* XL1-BLUE/Eco13.8 has been deposited with the American Type Culture Collection, 12301 Parklawn Drive, Rockville, Md., 20852, USA, on Jul. 19, 1995 under the terms of the Budapest Treaty, and has been given the deposit designation ATCC 69870.

EXAMPLE 4

Determination of the Nucleotide Sequence of the Xho3.4 DNA Fragment

The nucleotide sequence of the Xho3.4 DNA fragment obtained as described in EXAMPLE 3 was determined by the Sanger enzymatic sequencing method (Sequenase Version 2.0 kit, USB Inc.) using α-$^{35}$S-DATP label. This protocol is described below.

Approximately 5 μg of the Xho3.4 DNA fragment obtained as described in EXAMPLE 4, a plasmid containing this fragment, or a plasmid containing the 1.7 kb PstI-XhoI fragment of the Xho3.4 fragment was incubated in 0.2M NaOH, 0.2M EDTA at 37° C. for 30 min. The DNA was recovered by ethanol precipitation and washed with 70% (v/v) ethanol. To this precipitate were added 7 μl of deionized distilled water, 2 μl of Sequenase annealing buffer (5-fold concentration), 1 μl of primer to give a final composition of 40 mM Tris-HCl (pH 7.5), 20 mM MgCl$_2$, 50 mM NaCl, and 5 μg/L primer. This solution was heated to 65° C. for 2 min, and allowed to cool to room temperature below 30° C. over 30 min. The solution was then placed on ice. To this mixture were added 1 il of 0.1M DTT (dithiothreitol), 2 μl of labeling mixture (containing 1.5 μM dGTP, 1.5 μM dCTP, 1.5 μM dTTP), 0.5 ml of [α-$^{35}$S]dATP (10 μCi/ml, 1000 Ci/mmol), and 3 units of Sequenase version 2.0 T7 DNA polymerase. The solution was mixed well and allowed to react at room temperature for approximately 5 min. At the same time, four microtubes were individually labeled G, A, T, and C, and to these were added 2.5 μl of the respective ddNTP reaction solutions (composed of 80 μM dGTP, 80 μM DATP, 80 μM dTTP, 80 μM dCTP, 50 mM NaCl, and 8 μM of either dideoxy-dGTP, dideoxy-dATP, dideoxy-dTTP, or dideoxy-dCTP). These tubes were pre-incubated at 37° C. for 1 hr. Three point five μl of the completed labeling reaction mixture were then added to each of these four tubes, quickly mixed, and allowed to react for approximately 5 min at 37° C. The reaction was halted by the addition of 4 μl of reaction stop solution (containing 95% formamide, 20 mM EDTA, 0.05% bromophenol blue, and 0.05% xylene cyanol FF) and immediately mixed. The samples were analyzed by 8M urea-6% (w/v) polyacrylamide gel electrophoresis (approximately 65 watts, approximately 4 hr), the gel dried and exposed to Kodak XAR-5 film, and the sequence deter mined from the resultant autoradiogram. The resulting nucleotide sequence is shown in SEQ ID NO:1.

EXAMPLE 5

Biologically Functional Equivalent DNA Fragments Conferring Resistance to Porphyrin-Accumulating Type Herbicides Each of the nucleic sequences disclosed herein, or their biologically functional equivalents, can be used in accordance with the present invention. The phrase "biologically functional equivalents," as used herein, denotes nucleic acid sequences exhibiting the same or similar biological activity as the particular nucleic acid sequences described herein, i.e., when introduced into plant or algal cells in a functionally operable manner so that they are expressed, they confer resistance to porphyrin-accumulating type herbicides thereon.

For example, the nucleic acid sequences described herein can be altered by base substitutions, additions, or deletions to produce biologically functionally equivalent nucleic acids that encode proteins conferring resistance to porphyric herbicides in vitro and in vivo. In addition, due to the degeneracy of the genetic code, other DNA sequences that encode substantially the same amino acid sequences as described herein and confer resistance to porphyric herbicides in vitro and in vivo can be used in the practice of the present invention. These include, but are not limited to, nucleotide sequences comprising all or portions of the genomic DNAs described herein or the corresponding mRNAs or cDNAs that are altered by the substitution of different codons that encode a physiologically functionally equivalent amino acid residue within the protein sequence, thus producing a silent change. Similarly, the proteins conferring porphyric herbicide resistance, or derivatives thereof, encoded by the present invention include, but are not limited to, those containing all of the amino acid sequences encoded by the DNA sequences substantially as described herein, including altered sequences in which functionally equivalent amino acid residues are substituted for residues within the sequence, resulting in a silent change. For example, one or more amino acid residues within the sequence can be substituted with another amino acid of similar polarity which acts as a functional equivalent, resulting in a silent alteration. Substitutes for an amino acid within the sequence may be selected from other members of the class to which the amino acid belongs. For example, fungible nonpolar (hydrophobic) amino acids include alanine, leucine, isoleucine, valine, proline, phenylalanine, tryptophan, and methionine. Fungible polar neutral amino acids include glycine, serine, threonine, cysteine, tyrosine, asparagine, and glutamine. Fungible positively charged (basic) amino acids include arginine, lysine, and histidine. The negatively charged (acidic) amino acids include aspartic acid and glutamic acid.

The variants of the genomic DNAs, the corresponding mRNAs or cDNAs, and proteins contemplated herein should possess more than 75% homology, preferably more than 85% homology, and most preferably more than 95% homology, to the naturally occurring genomic DNAs, the corresponding mRNAs or cDNAs, and proteins discussed herein. To determine this homology, two proteins (or nucleic acids) are aligned so as to obtain a maximum number of matched residues using gaps and inserts. Homology (of two proteins) is determined as the result of the number of matched amino acids divided by the number of total amino acids plus gaps and inserts, multiplied by 100.

Biologically functional equivalents to the nucleic acid fragments disclosed herein can be created by mutagenesis techniques such as those described, for example, in Osuna, J., Flores, H., and Soberon, X. (*Critical Reviews in Microbiology* 20:107–116 (1994)), and selected for by transformation and screening of Chlamydomonas as described in EXAMPLE 2.

EXAMPLE 6

Isolation of DNA Fragments That Confer Resistance to Porphyrin-Accumulating Type Herbicides From Organisms Other Than *Chlamydomonas reinhardtii*

Degenerate oligonucleotide primers based on the deduced amino acid sequence of a cDNA corresponding to the RS-3 gene from *Chlamydomonas reinhardtii* can be synthesized and used to isolate the equivalent gene or cDNA from eubacteria, cyanobacteria, algae, and higher plants. PCR technology employing reverse transcriptase (Kawasaki, E. S. *PCR Protocols*, Ch. 3, p. 21, Innis et al., eds., Academic Press, San Diego, (1990)) and these degenerate oligonucleotides can be used to amplify the equivalent cDNAs from algae and higher plants, and these can be easily cloned in appropriate transformation/expression vectors for dicots such as pBIN described by Bevan, M. (*Nucl. Acids Res.* Vol. 12, p. 8711 (1984)) or pZ597 as described by Svab, Z. et al. (*Plant Mol. Biol.* Vol. 14, p. 197 (1990)), or for monocots using pDB1 described by Becker, D. et al. (*Plant J.*, Vol. 5, p. 299 (1994)) or pBARGUS described by Vasil, V. et al. [*Bio/Technology*, Vol. 10, p. 667 (1992)). Transformed plants expressing the cDNAs in these vectors can be isolated using established procedures as described below. Alternatively, the degenerate oligonuceotides can be used as probes to screen cDNA libraries from crop plants in lambda phage vectors such as λZapII (Stratagene). The corresponding cDNA can be transferred to an appropriate transformation/expression vector for introduction into monocot or dicot crop plants as described below. In the case of eubacteria and cyanobacteria, the degenerate oligonucleotides can be used to screen genomic libraries directly, and the appropriate coding sequences can be transferred into one of these transformation/expression vectors for crop plants as described below.

EXAMPLE 7

Transformation of Crop Plants and Algae to Porphyrin-Accumulating Type Herbicide Resistance The research described herein has identified DNA fragments that are able to confer resistance to porphyric herbicides onto plants and algae. Crop plants can be made resistant to porphyric herbicides by the introduction therein of these DNA fragments or their biologically functional equivalents. This invention will permit the use of porphyric herbicides during crop cultivation, and thus facilitate weed control and cultivation management on such crops.

Since the Chlamydomonas rs-3 resistance mutation is dominant (Sato, R. et al., ACS Symposium Series, Vol. 559, *Porphyric Pesticides*, S. O. Duke and C. A. Rebeiz, eds., Chapter 7, p. 91 (1994)), a full length cDNA corresponding to the subject DNA fragments under the control of the appropriate upstream and downstream regulatory sequences can be introduced into crop plants that lack resistance to porphyrin-accumulating type herbicides, so the RS-3 resistance gene can be utilized to generate crop plants resistant to porphyric herbicides.

In the case of dicot crop species, the chimeric RS-3 resistance construct can be inserted into a binary Agrobacterium vector such as pBIN described by Bevan, M. (*Nucl. Acids Res.* Vol. 12, p. 8711 (1984)) or pZ597 as described by Svab, Z. et al. (*Plant Mol. Biol.* Vol. 14, p. 197 (1990)), transferred into Agrobacterium by triparental mating according to Hoekema, A. et al. (*Nature* Vol. 303, p. 197 (1983)), and transformed into leaf discs of an agriculturally desirable cultivar by co-cultivation on medium containing carbenicillin and kanamycin. Shoots can be regenerated from kanamycin-resistant calli, and induced to form roots using standard plant tissue culture protocols (Bevan, M. *Nucl. Acids Res.* Vol. 12, p. 8711 (1984)). Kanamycin-resistant plants can be assayed for levels of resistance to porphyric herbicides, and the expected dominant 3:1 segregation of resistance verified in crosses to sensitive cultivars. Depending on the breeding system for a particular crop species, the herbicide-resistant transformants can be propagated by self pollination or backcrossed to the sensitive cultivar to establish a pure breeding, herbicide-resistant line. Examples of dicotyledonous crop plants to which this method can be applied include alfalfa, beans, cabbage, carrots, clover, cotton, various cucurbits, flax, peas and other agronomically important legumes, peanuts, peppers, potatoes, soybeans, sugar beets, sunflower, tobacco, and tomatoes.

In the case of monocot crop species, the full length RS-3 cDNA can be inserted in a monocot expression vector such as pDBl described by Becker, D. et al. (*Plant J.*, Vol. 5, p. 299 (1994)) or pBARGUS described by Vasil, V. et al. (*Bio/Technology*, Vol. 10, p. 667 (1992)) fused to the Adh1 promoter and intron or the Act1 promoter and to the nos terminator replacing the GUS gene in the constructs. Depending on the species, the chimeric plasmid can be introduced into embryogenic calli, immature embryos, scutellar tissue, immature inflorescences, microspores, or protoplasts by biolistic transformation, and calli, shoots, and plants regenerated under selective conditions in the presence of glufosinate to which the bar gene product encoded by both plasmids confers resistance. Glufosinate-resistant transgenic plants can then be assayed for levels of resistance to porphyric herbicides, and the expected dominant 3:1 segregation verified in crosses to sensitive cultivars. Depending on the breeding system for a particular crop species, the herbicide-resistant transformants can be propagated by self pollination or backcrossed to the sensitive cultivar to establish a pure breeding, herbicide-resistant line. Examples of monocotyledonous crop plants to which this method can be applied include barley, corn, forage crops, oats, onions, rice, rye, sorghum, sugar cane, and wheat.

If such crop plants that have thereby acquired resistance to porphyric herbicides are cultivated, the utilization of these herbicides on these crop plants becomes feasible. This should allow for simpler and more effective weed management, and increase the value of these herbicides in agricultural use. Furthermore, by using the subject DNA fragments as probes, it should be possible to identify other DNA fragments in crop plants that exhibit a high degree of sequence homology to the subject DNA fragments. This should make it possible to assess qualitatively and/or quantitatively whether a given crop plant will be resistant to porphyric herbicides prior to their actual treatment with such herbicides. In addition, this gene could be used as a resistance-type genetic marker in plant genetic engineering research and plant molecular biology/biotechnology, and should thus have significant industrial application.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An isolated, purified DNA, having the following characteristics:
   a) said DNA comprises a nucleotide sequence of a DNA fragment having a molecular size of approximately 3.4 kb, said DNA fragment being obtained from a strain of the unicellular green alga *Chlamydomonas reinhardtii* that exhibits resistance to porphyrin-accumulating type herbicides;
   b) said DNA contains restriction sites for XhoI, PstI, PstI, PstI, PstI, PstI, BamHI, SalI, SalI, and XhoI, and has a restriction site map as shown in FIG. 1(a); and
   c) said DNA confers resistance to porphyrin-accumulating type herbicides in algal cells when expressed therein.

2. The isolated, purified DNA according to claim 1, having the following characteristics:
   a) said DNA comprises a nucleotide sequence of a DNA fragment having a molecular size of approximately 9.9 kB; and
   b) said DNA contains restriction sites for EcoRI, XhoI, PstI, PstI, PstI, PstI, PstI, BamHI, SalI, SalI, XhoI, and HindIII, and has a restriction site map as shown in FIG. 1(b).

3. The isolated, purified DNA according to claim 1, having the following characteristics:
   a) said DNA comprises a nucleotide sequence of a DNA fragment having a molecular size of approximately 10.0 kB; and
   b) said DNA contains restriction sites for EcoRI, XhoI, PstI, PstI, PstI, PstI, PstI, BamHI, SalI, SalI, XhoI, HindIII, and KpnI, and has a restriction site map as shown in FIG. 1(c).

4. The isolated, purified DNA according to claim 1, having the following characteristics:
   a) said DNA comprises a nucieotide sequence of a DNA fragment having a molecular size of approximately 13.8 kB; and
   b) said DNA contains restriction sites for EcoRI, XhoI, PstI, PstI, PstI, PstI, PstI, BamHI, SalI, SalI, XhoI, HindIII, BamHI, SalI, HindIII, and KpnI, and has a restriction site map as shown in FIG. 1(d).

5. An isolated, purified DNA comprising the nucleotide sequence shown in SEQ. ID. NO.: 1.

6. A plasmid containing the DNA of any one of claims 1, 2, 3, 4 or 5.

7. A microorganism containing:
   (a) the plasmid of claim 6, or
   (b) the DNA of any one of claims 1, 2, 3, 4 or 5.

* * * * *